United States Patent

Borland et al.

Patent Number: 5,167,864
Date of Patent: Dec. 1, 1992

[54] AMINE OXIDE SURFACTANT COMPOSITIONS

[75] Inventors: James E. Borland; Terry Crutcher; Joe D. Sauer; Kim R. Smith, all of Baton Rouge, La.

[73] Assignee: Ethyl Corporation, Richmond, Va.

[21] Appl. No.: 787,238

[22] Filed: Nov. 4, 1991

Related U.S. Application Data

[63] Continuation-in-part of Ser. No. 698,539, May 10, 1991, abandoned.

[51] Int. Cl.$^5$ .................. B01F 17/00; B01F 17/22
[52] U.S. Cl. .................. 252/357; 252/547; 252/DIG. 3; 252/DIG. 14
[58] Field of Search ........... 252/355, 353, 550, 554, 252/547, DIG. 3, DIG. 14, 357

[56] References Cited

U.S. PATENT DOCUMENTS

| | | | |
|---|---|---|---|
| 4,256,611 | 3/1981 | Egan et al. | 252/548 |
| 4,264,479 | 4/1981 | Flanagan | 252/524 |
| 4,416,793 | 11/1983 | Barrat et al. | 252/531 |
| 4,588,514 | 5/1986 | Jones et al. | 252/98 |
| 4,654,158 | 3/1987 | Shepherd Jr. | 252/91 |
| 4,930,953 | 7/1990 | Pena et al. | 424/70 |
| 5,062,973 | 11/1991 | Kellett | 252/8.25 |
| 5,075,501 | 12/1991 | Borland et al. | 564/297 |

*Primary Examiner*—Richard D. Lovering
*Assistant Examiner*—N. Bhat
*Attorney, Agent, or Firm*—Patricia J. Hogan

[57] ABSTRACT

Surfactant mixtures which have performance and/or cost advantages over either component alone consist of 5–95% by weight of an amine oxide corresponding to the formula RR'R"NO in which R is a primary alkyl group containing 6–24 carbons and R' and R" are independently selected from methyl, ethyl, and 2-hydroxyethyl and 95–5% by weight of a fatty acid alkanolamide. Preferred mixtures are those in which the amine oxide is N-tetradecyldimetylamine oxide and the alkanolamide is cocodiethanolsuperamide.

14 Claims, No Drawings

AMINE OXIDE SURFACTANT COMPOSITIONS

CROSS-REFERENCE TO RELATED APPLICATION

This application is a continuation-in-part of copending application Ser. No. 698,539, filed May 10, 1991 now abandoned.

FIELD OF INVENTION

This invention relates to surfactant compositions and more particularly to such compositions which are mixtures of amine oxides and alkanolamides.

BACKGROUND

It is known that various surfactants have been found to be useful in cleaning compositions, such as shower gels, shampoos, and light duty detergents (e.g., dish detergents) — compositions in which good foamability is a prerequisite for consumer approval. The surfactants which have been used to the greatest extent in such compositions are anionic surfactants, such as alkyl sulfates, alkyl ether sulfates, sulfonates, sulfosuccinates, and sarcosinates.

Although the use of anionic surfactants in these compositions permits the attainment of desirable characteristics, including good foamability, it would be beneficial to find other surfactants which could provide equal or better performance at a lower cost. However, other known surfactants, such as amine oxides, betaines, and alkanolamides, are either more costly than the anionic surfactants or give poorer performance, e.g., smaller foam volume, when substituted for the anionic surfactants.

It is sometimes advantageous to use mixtures of surfactants in cleaning compositions when the surfactants can serve different functions, e.g., one serving to improve foamability and another serving to adjust viscosity. However, known surfactant mixtures typically provide a compromise between what can be achieved with the surfactant ingredients alone. Thus, e.g., a mixture of (A) a more costly surfactant which provides good foamability, foam density, or viscosity by itself with (B) a less expensive surfactant which provides poorer foamability, foam density, or viscosity by itself will provide an intermediate foamability, foam density, or viscosity.

SUMMARY OF INVENTION

It has been found that a mixture of 5-95% by weight of an amine oxide corresponding to the formula RR'R"NO in which R is a primary alkyl group containing 6-24 carbons and R' and R" are independently selected from methyl, ethyl, and 2-hydroxyethyl and 95-5% by weight of a fatty acid alkanolamide provides performance advantages and/or cost advantages over either component of the surfactant mixture alone.

DETAILED DESCRIPTION

Amine oxides which can be used in the practice of the invention are compounds corresponding to the formula RR'R"NO in which R is a primary alkyl group containing 6-24 carbons, preferably 10-18 carbons, and R' and R" are independently selected from methyl, ethyl, and 2-hydroxyethyl. The preferred amine oxides are those in which the primary alkyl group has a straight chain in at least most of the molecules, generally at least 70%, preferably at least 90% of the molecules; and the amine oxides which are especially preferred are those in which R contains 10-18 carbons and R' and R" are both methyl.

Exemplary of the preferred amine oxides are the N-hexyl-, N-octyl-, N-decyl-, N-dodecyl-, N-tetradecyl-, N-hexadecyl-, N-octadecyl-, N-eicosyl-, N-docosyl-, and N-tetracosyldimethylamine oxides, the corresponding amine oxides in which one or both of the methyl groups are replaced with ethyl or 2-hydroxyethyl groups, etc., and mixtures thereof. A particularly preferred amine oxide is N-tetradecyldimethylamine oxide.

Fatty acid alkanolamides which may be used in admixture with the amine oxides are the known nonionic surfactants usually designated as superamides, i.e., alkanolamides obtained by reacting a fatty acid, usually a fatty acid containing 8-18 carbons, with an alkanolamine in equimolar proportions. The preferred alkanolamide is cocodiethanolsuperamide.

Different proportionations of the ingredients of the surfactant mixtures provide different advantages, viz.:

(1) Amine oxide contents of 5-90% give higher viscosities and foam densities than can be achieved with either surfactant alone.

(2) Amine oxide contents of 45-95% give more foam than the alkanolamide alone at a lower cost/mL of foam than either component alone.

(3) Amine oxide contents of 65-95% give as much or more foam than either surfactant alone at a lower cost/mL of foam than either surfactant alone.

(4) Amine oxide contents of 90-95% give higher foam densities and more foam than either component of the mixture alone at a lower cost/mL of foam than either component alone.

When a synergistic improvement in viscosity is desired, the mixture should contain 5-90%, preferably 10-80%, more preferably 25-55%, and most preferably about 50% by weight of the amine oxide. Synergistic increases in foam density are obtained when the mixture contains 5-95%, preferably 20-85%, more preferably 40-80%, and most preferably about 75% of the amine oxide; synergism in foamability is achieved when the mixture contains >65%, preferably 70-90%, and most preferably about 75% by weight of the amine oxide.

Although synergism between two materials is never actually expected, the synergism between certain proportions of amine oxides and alkanolamides in foam production is particularly unexpected. When these components are used to form mixtures containing less than about 27% by weight of the amine oxide, the mixtures actually produce less foam than the alkanolamide alone, even though amine oxides alone provide more foam than alkanolamides.

Because of the poor foamability of amine oxide/alkanolamide mixtures containing the smaller amounts of amine oxide, the surfactant mixtures of the invention containing <30% by weight of amine oxide are not particularly attractive for use in applications requiring good foamability for customer approval. However, they can be usefully employed in other applications, such as hard surface cleaners.

The cost of the surfactant to be used in a formulation such as a cleaning composition is always a factor to be considered, of course; and the cost of a given amount of an amine oxide/alkanolamide mixture is always higher than the cost of the same amount of the alkanolamide because of the higher cost of amine oxides. However, as indicated above, the better performance of the mixtures can permit a given level of performance to be achieved with a smaller amount of surfactant; and that level of performance can thus be attained at a lower cost than when either component of the surfactant mixture is used alone.

Although the surfactant mixtures of the invention are also beneficial in their ability to provide higher viscosities and foam densities, their greatest advantage appears to be their ability to provide acceptable levels of foam more economically than the individual components of the mixtures. This characteristic of the mixtures makes them valuable for use in the cleaning compositions which require foaming for customer approval, e.g., shampoos, shower gels, and light duty detergents.

When employed in such compositions, the surfactant mixtures are utilized in an aqueous medium, which typically constitutes about 10-90% of the weight of the compositions; and they may be used in conjunction with other ingredients of the types conventionally used in the compositions. Such ingredients include, e.g., viscosity improvers, pH adjusters, colorants, pearlizing agents, clarifying agents, fragrances, preservatives, antioxidants, chelating agents, skin and hair conditioners, botanical extracts, and antibacterial agents.

The following examples are given to illustrate the invention and are not intended as a limitation thereof. Unless otherwise specified, quantities mentioned in the examples are quantities by weight.

EXAMPLE I

Prepare several aqueous surfactant solutions having a total surfactant content of 5% from N-tetradecyldimethylamine oxide and cocodiethanolsuperamide. The proportions of these surfactants used in preparing each of the solutions, as well as the viscosities of the solutions, are shown in Table I.

TABLE I

| % Amine oxide | % Alkanolamide | Viscosity (mPa.s) |
|---|---|---|
| 100 | 0 | 23 |
| 90 | 10 | 52 |
| 80 | 20 | 84 |
| 55 | 45 | 157 |
| 50 | 50 | 177 |
| 25 | 75 | 150 |
| 10 | 90 | 84 |
| 5 | 95 | 52 |
| 0 | 100 | 37 |

EXAMPLE II

Prepare several aqueous solutions having a total surfactant content of 5% from N-tetradecyldimethylamine oxide and cocodiethanolsuperamide. Test each solution to show the density of the foam it can produce by placing 25 ML of the solution in a 100 mL blender cup, mixing for 15 seconds, transferring the foam to a tared graduated cylinder, and calculating the foam density. The proportions of the surfactants used in preparing each of the solutions and the foam densities obtained are shown in Table II.

TABLE II

| % Amine Oxide | % Alkanolamide | Density (g/mL) |
|---|---|---|
| 100 | 0 | 0.188 |
| 75 | 25 | 0.711 |
| 50 | 50 | 0.655 |
| 25 | 75 | 0.538 |
| 0 | 100 | 0.223 |

EXAMPLE III

Dissolve varying amounts of N-tetradecyldimethylamine oxide and cocodiethanolsuperamide in hard water (200 ppm as $CaCO_3$) to provide solutions having a total surfactant content of 0.1%. Measure the foamability of the surfactants by (1) placing 30 mL of each of the solutions in a 100 mL stoppered graduated cylinder, (2) inverting the cylinder ten times, (3) measuring the foam height, (4) repeating steps 1-3 twice, and (5) calculating the average of the three measurements. The proportions of amine oxide and alkanolamide used in preparing each of the solutions and the foam heights obtained from them are shown in Table III.

TABLE III

| % Amine Oxide | % Alkanolamide | Foam Height (mL) |
|---|---|---|
| 100 | 0 | 33 |
| 95 | 5 | 33.8 |
| 90 | 10 | 34.6 |
| 75 | 25 | 37 |
| 70 | 30 | 35 |
| 65 | 35 | 33 |
| 50 | 50 | 27 |
| 45 | 55 | 24.8 |
| 25 | 75 | 16 |
| 0 | 100 | 17 |

What is claimed is:

1. A surfactant mixture consisting of 5-95% by weight of an amine oxide corresponding to the formula RR'R"NO in which R is a primary alkyl group containing 6-24 carbons and R' and R" are independently selected from the group consisting of methyl, ethyl, and 2-hydroxyethyl and 95-5% by weight of a superamide fatty acid alkanolamide.

2. The surfactant mixture of claim 1 wherein R is a primary alkyl group containing 10-18 carbons, R' and R" are methyl, and the alkanolamide contains an alkyl group of 8-18 carbons.

3. The surfactant mixture of claim 2 wherein the amine oxide is N-tetradecyldimethylamine oxide and the alkanolamide is cocodiethanolsuperamide.

4. The surfactant mixture of claim 3 having an amine oxide content of at least 30% by weight.

5. The surfactant mixture of claim 4 having an amine oxide content of at least 45% by weight.

6. The surfactant mixture of claim 5 having an amine oxide content of at least 65% by weight.

7. The surfactant mixture of claim 6 wherein the amine oxide content is 70-90% by weight.

8. The surfactant mixture of claim 7 wherein the amine oxide content is about 75% by weight.

9. The surfactant mixture of claim 3 wherein the amine oxide content is 20-85% by weight.

10. The surfactant mixture of claim 9 wherein the amine oxide content is 40-80% by weight.

11. The surfactant mixture of claim 3 wherein the amine oxide content is 5-90% by weight.

12. The surfactant mixture of claim 11 wherein the amine oxide content is 10-80% by weight.

13. The surfactant mixture of claim 12 wherein the amine oxide content is 25-55% by weight.

14. The surfactant mixture of claim 13 wherein the amine oxide content is about 50% by weight.

* * * * *